United States Patent [19]

Wong

[11] Patent Number: 5,370,870
[45] Date of Patent: Dec. 6, 1994

[54] METHOD FOR PROTECTION AGAINST REACTIVE OXYGEN SPECIES

[75] Inventor: Grace H. W. Wong, South San Francisco, Calif.

[73] Assignee: Genentech, Inc., South San Francisco, Calif.

[21] Appl. No.: 76,087

[22] Filed: Jun. 11, 1993

Related U.S. Application Data

[63] Continuation of Ser. No. 602,850, Oct. 25, 1990, abandoned, which is a continuation-in-part of Ser. No. 418,010, Oct. 6, 1989, Pat. No. 5,200,176.

[51] Int. Cl.$^5$ .............................................. A61K 37/02
[52] U.S. Cl. ...................................... 424/85.1; 514/2; 514/8; 514/12; 530/351; 930/144; 424/85.2
[58] Field of Search ........................... 424/85.1, 85.2; 530/387, 351; 514/2, 8, 12; 930/144

[56] References Cited

U.S. PATENT DOCUMENTS

| | | |
|---|---|---|
| 4,808,402 | 2/1989 | Leibovich et al. . |
| 4,846,782 | 7/1989 | Bonnem . |
| 4,861,587 | 8/1989 | Urbaschek et al. ................. 424/85.1 |
| 4,985,241 | 1/1991 | Zimmerman et al. . |

FOREIGN PATENT DOCUMENTS

| | | |
|---|---|---|
| 164965 | 12/1985 | European Pat. Off. . |
| 168214 | 1/1986 | European Pat. Off. ........ C07K 3/18 |
| 235906 | 9/1987 | European Pat. Off. . |
| 239289 | 9/1987 | European Pat. Off. . |
| 259863 | 3/1988 | European Pat. Off. ...... A61K 37/02 |
| 284105 | 9/1988 | European Pat. Off. ...... C12N 15/00 |
| 0340005 | 4/1989 | European Pat. Off. . |
| 357240 | 3/1990 | European Pat. Off. . |
| WO91/15227 | 10/1991 | WIPO . |

OTHER PUBLICATIONS

Lowe et al. *DNA* 8(5):351–59 (1989).
Slordal et al. *Eur J. Haematol* 43:428–34 (1989).
Berkow, R. et al., "Enhancement of Neutrophil Superoxide Production by Preincubation with Recombinant Human Tumor Necrosis Factor," *J. Immunol.* 139(1): 3783–3791 (1987).
Braquet, P. et al., "Role of Cytokines and Platelet-Activating Factor in Microvascular Immune Injury," *Int. Arch. Allergy Appl. Immunol.* 88: 88–100 (1989).
Carswell, E. et al., "An Endotoxin-Induced Serum Factor that Causes Necrosis of Tumors," *Proc. Nat. Acad. Sci, USA* 73(9): 3666–3670 (1975).
Clark, I and Chaudhri, G., "Interplay of Reactive Oxygen Species and Tumor Necrosis Factor in Tissue Injury," *J. Cell. Biochem.*, UCLA Symposia on Molecular and Cellular Biology, Supplement 12a: 8023 (1988).
Cross, A. et al., "Pretreatment with Recombinant Murine Tumor Necrosis Factor α/Cachectin and Murine Interleukin 1 α Protects Mice from Lethal Bacterial Infection," *J. Exp. Med.* 169: 2021–2027 (1989).
Decker, T. and Lohmann-Matthes, M., "A Quick and Simple Method for the Quantitation of Lactate Dehydrogenase Release in Measurements of Cellular Cytotoxicity and Tumor Necrosis Factor (TNF) Activity," *J. Immunol.* 15: 61–69 (1988).
Galaris, D. et al., "Mechanisms of Reoxygenation Injury in Myocardial Infarction: Implications of a Myoglobin Redox Cycle," *Biochem. Biophys. Res. Comm.* 160(3): 1162–1168 (1989).
Gordon, T. and Sheppard, D., "Tumor Necrosis Factor Inhibits a Polymorphonuclear Leukocyte-Dependent (List continued on next page.)

Primary Examiner—Garnette D. Draper
Assistant Examiner—Shelly Guest Cermak
Attorney, Agent, or Firm—Ginger Dregar

[57] ABSTRACT

Methods suitable for the protection inhibtion and prevention of the deleterious effects of reactive oxygen species are provided, wherein an effective amount of a protective agent(s) selected from the group of tumor necrosis factor-alpha and -beta, growth hormone, IL-1, and D-factor is administered. Treatment of tissues and organs to be transplanted is described. Perfusion solutions and the preparation of perfused, excised tissue are described.

24 Claims, 5 Drawing Sheets

OTHER PUBLICATIONS

Airway Edema in Guinea Pigs," *J. Appl. Physiol.* 64: 1688–1692 (1988).

Hahn, T. et al., "Use of Monoclonal Antibodies to a Human Cytotoxin for Its Isolation and for Examining the Self-Induction of Resistance to this Protein," *Proc. Natl. Acad. Sci. USA* 82: 3814–3818 (1985).

Hellqvist et al., "Interleukin I Induces New Protein Formation in Isolated Rat Islets of Langerhans," Dialog Information Services, File 155, Medline 66–91, Dialog Accession No. 06998107.

Hjalmarsson, K. et al., "Isolation and Sequence of Complementary DNA Encoding Human Extracellular Superoxide Dismutase," *Proc. Natl. Acad. Sci. USA* 84: 6340–6344 (1987).

Holtmann and Wallach, "Down Regulation of the Receptors for Tumor Necrosis Factor By Interleukin 1 and 4$\beta$-Phorbol-12-Myristate-13-Acetate," *J. Immunol.* 139(4): 1161–1167 (1987).

Jacob, C. and McDevitt, H., "Tumour Necrosis Factor-$\alpha$ in Murine Autoimmune 'Lupus' Nephritis," *Nature* 331: 356–358 (1988).

Kalayoglu, M. et al., "Extended Preservation of the Liver for Clinical Transplantation," *The Lancet,* Mar. 19, 1988 pp. 617–619.

Leurs, R., et al., "Inhibition of Superoxide Anion Radical Production by Ebselen (PZ51) and Its Sulfur Analogue (PZ25) in Guinea Pig Alveolar Macrophages," *Biochem. Int'l.* 18(2): 295–299 (1989).

Lowe et al., "Genomic Cloning and Heterologous Expression of Human Differentiation-Stimulating Factor," *DNA* 8(5): 351 (1989).

Maessen, J. et al., "Sensitivity of Ischemically Damaged Kidneys to Inflammatory Reactions," *Transplantation Proceedings* 21(1): 1261–1262 (1989).

Matsubara, T. and Ziff, M., "Increased Superoxide Anion Release from Human Endothelial Cells in Response to Cytokines," *J. Immunol.* 137(10): 3295–3298 (1986).

Moreau, J. et al., "Leukaemia Inhibitory Factor is Identical to the Myeloid Growth Factor Human Interleukin for DA Cells," *Nature* 336: 690 (1988).

Neta, R. et al., "Interdependence of the Radioprotective Effects of Human Recombinant Interleukin 1$\alpha$, Tumor Necrosis Factor $\alpha$, Granulocyte Colony-Stimulating Factor, and Murine Recombinant Granulocyte-Macrophage Colony-Stimulating Factor," *J. Immunol.* 140(1): 108–111 (1988).

Neta, R. and Oppenheim, J., "Cytokines in Therapy of Radiation Injury," *Blood* 72(3): 1093–1095 (1988).

Neta, R. et al., "Comparison of the In Vivo Effects of rIL-1 and rTNF in Radioprotection, Induction of CSF and of Acute Phase Reactants," *Fed. Proc.* 46(4): 1200 (Abstract) (1987).

Neta, R. et al., "Interleukin 1 is a Radioprotector," *J. Immunol.* 136(7): 2483–2485 (1986).

Neta, R., "Role of Cytokines in Radioprotection," *Pharmac. Ther.* 39: 261–266 (1988).

Neta, R. et al., "Cytokines in Radioprotection. Comparison of the Radioprotective Effects of IL-1 to IL-2, GM-CSF and IFN $\gamma$," *Lymphokine Research* 5,(Suppl. 1): S105–S110 (1986).

Oda, T. et al., "Oxygen Radicals in Influenza-Induced Pathogenesis and Treatment with Pyran Polymer-Conjugated SOD," *Science* 244: 974–976 (1989).

Omar, B. and McCord, J., "The Cardioprotective Effect of Mn-Superoxide Dismutase is Lost at High Doses in the Postischemic Isolated Rabbit Heart," *Free Radical Biology and Medicine* 9: 473–478 (1990).

Omar, B. et al., "Cardioprotection by Cu,Zn-Superoxide Dismutase is Lost at High Doses in the Reoxygenated Heart," *Free Radical Biology and Medicine* 9: 465–471 (1990).

Omar, R. et al., "Antioxidant Enzymes and Survival of Normal and Simian Virus 40-transformed Mouse Embryo Cells after Hyperthermia," *Cancer Research* 47: 3473–3476 (1987).

Palladino, M. et al., "$\gamma$-Irradiation-Induced Mortality: Protective Effect of Protease Inhibitors in Chickens and Mice," *Int. J. Radiat. Biol.* 41(2): 183–191 (1982).

Saez, J. et al., "Superoxide Dismutase Protects Cultured Neurons Against Death by Starvation," *Proc. Natl. Acad. Sci. USA* 84: 3056–3059 (1987).

Schutze, S. et al., "Tumor Necrosis Factor-Induced Changes of Gene Expression in U937 Cells," *J. Immunol.* 140(9): 3000–3005 (1988).

(List continued on next page.)

OTHER PUBLICATIONS

Shalaby, M. et al., "Receptor Binding and Activation of Polymorphonuclear Neutrophils by Tumor Necrosis Factor-Alpha," *J. Leukocyte Biol.* 41: 196–204 (1987).

Slordal et al., "Radioprotection by Murine and Human Tumor-Necrosis Factor: Dose-Dependent Effects on Hematopoiesis in the Mouse," *Eur. J. Haematol.* 43: 428–434 (1989).

Sugarman, B. et al., "Recombinant Human Tumor Necrosis Factor-α: Effects on Proliferation of Normal and Transformed Cells In Vitro," *Science* 230: 943–945 (1985).

Sullivan, G. et al., "Inhibition of the Inflammatory Action of Interleukin-1 and Tumor Necrosis Factor (alpha) on Neutrophil Function by Pentoxifylline," *Infection and Immunity* 56(7): 1722–1729 (1988).

Taylor, M. et al., "Pharmacological Protection of Reoxygenation Damage to In Vitro Brain Slice Tissue," *Brain Research* 347: 268–273 (1985).

Tiegs, G. et al., "Tumor Necrosis Factor is a Terminal Mediator in Galactosamine/Endotoxin-Induced Hepatitis in Mice," *Biochem. Pharm. 38(4): 627–631 (1989)*.

Tsujimoto, M. et al., "Tumor Necrosis Factor Provokes Superoxide Anion Generation From Neutrophils," *Biochem. and Biophys. Res. Comm.* 137(3): 1094–1100 (1986).

Urbaschek, R. et al., "Tumor Necrosis Factor Induced Stimulation of Granulopoiesis and Radioprotection," *Lymphokine Research* 6(3): 179–186 (1979).

Wallach, D., "Preparations of Lymphotoxin Induce Resistance to Their Own Cytotoxic Effect," *J. Immunol.* 132(5): 2464–2469 (1984).

Walton, P. and Cronin, M., "Tumor Necrosis Factor-α Inhibits Growth Hormone Secretion from cultured Anterior Pituitary Cells," *Endocrinology* 125(2): 925–929 (1989).

White, C. et al., "Recombinant Tumor Necrosis Factor/Cachectin and Interleukin 1 Pretreatment Decreases Lung Oxidized Glutathione Accmulation, Lung Injury, and Mortality in Rats Exposed to Hyperoxia," *J. Clin. Invest.* 79: 1868 (1987).

Wong, G. and Goeddel, D., "Induction of Manganous superoxide Dismutase by Tumor Necrosis Factor: Possible Protective Mechanism," *Science* 242: 941–944 (1988).

Zimmerman et al., "Oxidative Damage in Murine Tumor Cells Treated In vitro by Recombinant Human Tumor Necrosis Factor," Dialog Information Services, File 155, Medline 66–91, Dialog Accession No. 06866198.

```
hdf   1 PLPITPVNATCAIRHPCH NNLMNQIRS QLAQLNGSANALFIL YYTAQGEP
mdf   1 PLPITPVNATCAIRHPCH GNLMNQIKN QLAQLNGSANALFIS YYTAQGEP hdf  51 FPNNLDKLCG PNVTDFPPFH ANGTEKA KLVELYRI VVLGTS LGNITRDQ
mdf  51 FPNNVEKLCA PNMTDFPSFH GNGTEKT KLVELYRM AYLSAS LTNITRDQ hdf 101 KILNPSALSLHS KLNATAD ILRGLLSNVLCRLCS KYHVGHVDVTYGPDT S
mdf 101 KVLNPTAVSLQV KLNATI DVMRGLLSNVLCRLCN KYRVGHVDVPPVPDH S hdf 151 GKDVFQ KKLGCQLLGK YKQI IAVL AQAF
mdf 151 DKEAFQR KKLGCQLLGT YKQV IS VVQAF
```

FIG. 3

METHOD FOR PROTECTION AGAINST REACTIVE OXYGEN SPECIES

BACKGROUND OF THE INVENTION

This application is a continuation of 07/602850, filed Oct. 25, 1990, now abandoned which is a continuation-in-part of U.S. Ser. No. 07/418,010, filed 6 Oct. 1989, now U.S. Pat. No. 5,200,176.

This invention relates to methods for inhibiting, preventing, protecting against or treating the deleterious effects of reactive oxygen species. The invention also relates to methods for protecting against injury to tissues from ischemia and reperfusion injury.

Superoxide radicals ($O_2^-$) and other highly reactive oxygen species such as hydrogen peroxide ($H_2O_2$) and hydroxyl radicals (referred to herein as reactive oxygen species or "ROS") are produced in vivo by enzymatic, spontaneous, and photochemical oxidation reactions. ROS are produced by mitochondria during electron transport. Other intracellular sources of $O_2^-$ and $H_2O_2$ are endoplasmic reticulum, peroxisomes, and nuclear and plasma membranes. Examples of disorders associated with the generation of ROS include: synovial inflammation induced by bacterial lipopolysaccharide endotoxin (LPS), inflammation caused by adjuvant-induced arthritis, bleomycin-induced lung fibrosis, reperfusion injury, transplantation rejection, hyperoxia, and any diseases caused by oxygen and light. It has been suggested that ROS may be involved in hyperthermic cell injury (Omar et al., Cancer Res. 47:3473, 1987), and that thermosensitivity is linked to a low rate of free radical removal.

Certain agents are capable of inducing superoxide or other oxygen free radicals. Such ROS activity may be determined by commonly used methods, such as their ability to induce guinea pig alveolar macrophages to produce reactive oxygen metabolites which are measurable by spectrometer at $A_{550-540nm}$ (Leurs et al., Biochemistry International 18 (2):295–299, 1989), or by known inflammatory or chemiluminescence test models. Agents which are known to enhance the production of ROS include but are not limited to the following commercially available compounds: inhibitors of glutathione synthesis such as buthionine sulfoximine, anthracyclines such as adriamycin (doxorubicin), adriamycinone (doxorubicinone), daunomycin, daunomycinone, daunorubicin, and daunorubicin derivatives such as 5-iminodaunorubicin, ubiquinone, Acid Blues 25, 80, and 41, Acid Green 25, anthraquinone and its derivatives such as 2-bromoanthraquine, 1,2-dihydroxyanthraquinone, 1,8-diaminoanthraquinone, 2,6-diaminoanthraquinone, 1,5-dichloroanthraquinone, 1,2-diaminoanthraquinone, and 2-chloro-anthraquinone, quinizarin, anthrarufin, quilalizarin, aloe-emodin and related compounds such as 5-nitro-aloe-emodin, 5-amino-aloe-emodin. 2-allylaloe-emodin, averufin, kalafungin, alizarin complexone dihydrate, quercetin dihydrate, acid black 48, procytoxid, leucotrofina, azimexon, and methoxycin-narnonitrile. These ROS inducing agents may be administered therapeutically, by intravenous or other methods as desired.

A group of metalloproteins known as superoxide dismutases (SOD) catalyze the oxidation-reduction reaction $2O_2^- + 2H^+ \rightarrow H_2O_2 + O_2$ and thus provide part of the defense mechanism against oxygen toxicity. Eukaryotic cells contain copper-zinc SOD, which is found predominantly in the cylosol, and MnSOD, which is found mainly in mitochondria. Extracellular SOD is found primarily in extracellular fluids such as plasma, lymph, and synovial fluid, but occurs also in tissues (Hjalmarsson et al., Proc. Natl. Acad. Sci. USA 84:6340, 1987).

The scientific literature suggests that SOD administration may be useful in a wide range of clinical applications. Potential applications include prevention of oncogenesis and of tumor promotion, treatment of inflammations, reduction of the cytotoxic and cardiotoxic effects of anticancer drugs, protection of ischemic tissues and protection of spermatozoa (EPO Appl. EP 0 284 105 A2). It has also been suggested that oxygen free radicals are involved in the pathogenesis of, and that SOD administration protects against, influenza virus infection (Oda et al., Science 244: 974–976, 1989).

Ischemia causes injury to cells, and if continued for a sufficient length of time, can kill them. Reperfusion after a brief period of ischemia, although beneficial in the long term, frequently results in an initial injury to the tissues upon reoxygenation, presumably through the formation and involvement of reactive oxygen species. This phenomenon has been described in the literature with heart, skin, intestine, pancreas, and variety of tissues. It is also important to protect against reoxygenation injury during thrombolytic therapy, and in the preservation of organs for transplantation.

D-Factor (hereafter "DF") is a known molecule. It is capable of directing the choice of neurotransmitter phenotype made by cultured rat sympathetic neurons, regulates the growth and differentiation of embryonic stem cells and myeloid cells and stimulates bone remodeling and acute-phase protein synthesis in hepatocytes. It has been termed DIA, DIF, DRF, HSFIII, human interleukin DA (HILDA) and LIF (leukemia inhibitory factor). This cytokine has been compared to IL-6 and TGF-beta in that it regulates function, growth and differentiation in the embryo and in the adult in many tissues and cell types, including monocytic cells, megakaryocytes, embryonal stem cells, hepatocytes, adipocytes, osteoblasts and neuronal cells. See Yarnamori et al., "Science" 246:1412 (1989), Lowe et at., "DNA" 8(5):351 (1989) and Abe et al., "J. Biol. Chem." 264(15):8941 (1989). DF also is known to induce differentiation of myeloid leukemia cells and therefore has been proposed in the art to be useful in the treatment of myeloid leukemias. DF is currently purified by complex methods not amenable to large scale commercial development (Hilton et al., "Analyt. Biochem." 179:359 [1988]). The use of DF for protection against injury from radiation or chemotherapy has been disclosed in U.S. Ser. No. 07/507,341 filed 10 April 1990, now abandoned.

Growth hormone (GH) and human growth hormone (hGH) are secreted in the pituitary. The mature form of hGH consists of 191 amino acids and has a molecular weight of about 22,000; its sequence and characteristics are set forth, for example, in Hormone Drugs, Geuriguian et al., U.S. Pat. Convention, Rockville Md. (1982), incorporated herein by reference.

hGH has been used for the treatment of hypopituitary dwarfism, and has been proposed for the treatment of burns, wound healing, dystrophy, bone knitting, diffuse gastric bleeding and pseudarthrosis. The major biological effect of GH is to promote growth. The organ systems affected include the skeleton, connective tissue, muscles, and viscera such as liver, intestine, and kidneys. Growth hormone exerts its action through interaction with specific receptors on cell membranes. Administration of growth hormone for treatment of pulmonary dysfunction and ventilator dependency has been proposed in U.S. Pat. No. 5,089,475 filed 7 Feb. 1989; in this application causes of pulmonary dysfunction are stated to include physical injury as well as naturally occurring diseases such as pulmonary obstruction, pneumonia, asthma, emphysema, cancers, autoimmune diseases, neurological disorders including stroke, and chest deformities.

Interleukin-1 (IL-1) is produced by activated macrophages. At least two types exist, designated $\beta$ and $\beta$ (March et al., Nature 315:641–647 (1985)). IL-1 mediates a wide range of biological activities; it has been found to stimulate fibroblast proliferation and to induce in these cells the synthesis of collagenase, prostaglandin $E_2$ and interferon beta-2, to decrease in adipocytes the activity of lipoprotein lipase, and to activate osteoclasts.

Tumor necrosis factors (TNFs) are polypeptides produced by mitogen-stimulated macrophages (TNF-$\alpha$) or lymphocytes (TNF-$\beta$) which are cytotoxic to certain malignantly transformed cells but not to certain normal cells (E. A. Carswell et al., Proc. Natl. Acad. Sci. U.S.A. 72:3666, 1975; B. J. Sugarman et al., Science 230:943, 1985; Schultze et al., J. Immunol. 140: 3000, 1988). TNF-$\alpha$ has been suggested to be responsible for wasting and cachexia in patients with cancer or severe infections, and both TNF-$\alpha$ and TNF-$\beta$ mediate many other biological effects. TNF is also known to induce MHC antigens. The inventors herein have reported that TNF induces MnSOD in various transformed and normal cell lines (Wong et al., Science 242:941, 1988).

TNF at certain dosages is known to trigger the generation of ROS in macrophages or neutrophils (Tsujimoto et al., Biochem. Biophys. Res. Commun. 137: 1094, 1986; Matsubara et al., J. Immunol. 137:3295, 1986; Shalaby et al., Leuk. Biol. 41:196, 1987; Berkow et al., J. Immunol. 139:3783, 1987). It has been suggested repeatedly in the literature that TNF at certain dosages enhances tissue injury caused by reactive oxygen species (see, e.g. Clark et al., J. Cell Biochem. Suppl. 12A, p. 40, Jan 1988; Sullivan et al., Infect. and Immunity 56(7): 1722–1729, 1988; and Tiegs et al., Biochem. Pharmacol. 38(4): 627–631, 1989).

The literature has reported that TNF-$\alpha$ and other cytokines such as IL-1 may protect against the deleterious effects of ionizing radiation produced during a course of radiotherapy, such as denaturation of enzymes, lipid peroxidation, and DNA damage (Neta et al., J. Immunol. 136(7):2483, 1987; Neta et al., Lymphokine Res. 5 et al., supra; Neta et al., Fed. Proc. 46:1200 (abstract), 1987; Urbaschek et al., Lymphokine Res. 6: 179, 1987; U.S. Pat. No. 4,861,587; Neta et al., J. Immunol. 140: 108, 1988), and that TNF treatment accelerates restoration of hematopoiesis in animals compromised by sublethal doses of cytotoxic drugs or irradiation (Neta, et al., Blood 72(3):1093, 1988). A recent article reported that pretreatment with TNF protects mice from lethal bacterial infection (Cross et al., J. Exp. Med. 169:2021–2027, 1989). It has also been suggested that administration of subdeleterious amounts of TNF and/or IL-1 may modulate the deleterious effect of subsequent TNF and/or IL-1 administration; this reference further suggests that ionizing radiation may be administered as a sensitizing agent (EPO Appl. EP 0 259 863 A2). It has also been reported that pretreatment of cells with low levels of either TNF or IL-1 can confer resistance to killing by subsequent treatment with TNF-$\alpha$ and cycloheximide in combination (Wallach, J. Immunol. 132:2464, 1984; Hahn et al., Proc. Natl. Acad. Sci. U.S.A. 82:3814, 1985; Holtamann et al., J. Immunol 139:1161, 1987). It has been suggested that inadequate endogenous levels of TNF may be involved in the development of diabetes and of lupus erythematosus (Jacob et al., Nature 331:356–358, 1988).

Saez et al., Proc. Natl. Acad. Sci. USA 84: 3056–3059, 1987, have shown that SOD protects cultured neurons against death by glucose deprivation. Tsan et al., J. Appl. Physiol. 68(3): 1211–1219, 1990, has recently confirmed that tracheal insufflation of TNF (and IL-1 in unpublished data) protects rats against oxygen toxicity.

White et al., J. Clin. Invest, 79: 1868–1873, 1987, have shown that pretreatment with a combination of TNF and IL-1 decreases lung injury and mortality in rats exposed to hyperoxia, but indicate that, with i.p. injection, either TNF or IL-1 alone protected the rats only comparable to saline.

It is an object of this invention to provide methods for protecting ischemic tissues, such as those tissues, bones or organs to be transplanted from a donor to a recipient patient, or those tissues whose oxygen supply has been blocked, from the effects of ROS.

It is a further object herein to provide methods to inhibit, prevent or treat reperfusion injury, bronchopulmonary dysplasia, stroke, arteriolosclerosis, atherosclerosis, myocardial infarct, inflammatory autoimmune diseases, viral infection, inflammation-induced arthritis, hyperoxia, sepsis, diabetes, influenza, multiple sclerosis, hyperbaric treatment after premature birth, acquired immunodeficiency syndrome, transplant rejection or transplantation injury, bleomycin-induced lung fibrosis, synovial inflammation induced by bacterial LPS endotoxin, lung injury resulting from immune complexes, hyperbaric treatment of cancer, kidney disease, Parkinson's disease, sickle cell anemia, sickle cell trait, alcoholic or non-alcoholic cirrhosis, or other diseases associated with toxic ROS.

Another object of this invention is to supply perfusion solutions and excised, perfused tissues for transplant.

These and other objects of the invention will be apparent from consideration of the specification as a whole.

SUMMARY OF THE INVENTION

Unexpectedly, and contrary to the suggestions in the literature, the present inventors have discovered that treatment with certain doses of TNF and/or IL-1, alone or in combination with growth hormone and/or D-factor, protect against ROS damage.

The objects of this invention are accomplished by methods utilizing these effects of the protective agent(s) TNF, IL-1, GH and DF. In one preferred method, a patient at risk for reperfusion injury is treated with an effective but sub-deleterious amount of at least one of these agents before, at, or after, but preferably prior to reperfusion. In another embodiment, a patient with a condition or disease associated with ROS (as described above) is treated with a dose of at least one of these agents which is effective at preventing, inhibiting or treating that condition.

Other preferred embodiments relate to tissue transplant. In one embodiment, ischemic tissue is protected by the administration of an effective amount of at least one of TNF, GH, DF, and/or IL-1 prior to reperfusion of the tissue. This ischemic tissue may be treated prior to or after removal from a donor, and before or after it is transferred to or implanted in a recipient patient.

This invention also encompasses perfusion solutions comprising at least one of the above protective agent(s) in a pharmaceutically acceptable excipient, as well as perfused, excised tissues, where the tissues are perfused with such a perfusion solution.

In an alternate embodiment, the protective agent(s) is administered to a tissue donor prior to preparation for removal of the tissue.

DESCRIPTION OF THE DRAWINGS

FIG. 3 depicts the mature amino acid sequences for human (H) (Sequence ID No. 1) and murine (M) (Sequence ID No. 2) D-factor. Areas of homology are boxed.

DETAILED DESCRIPTION

Figures 1, 2:
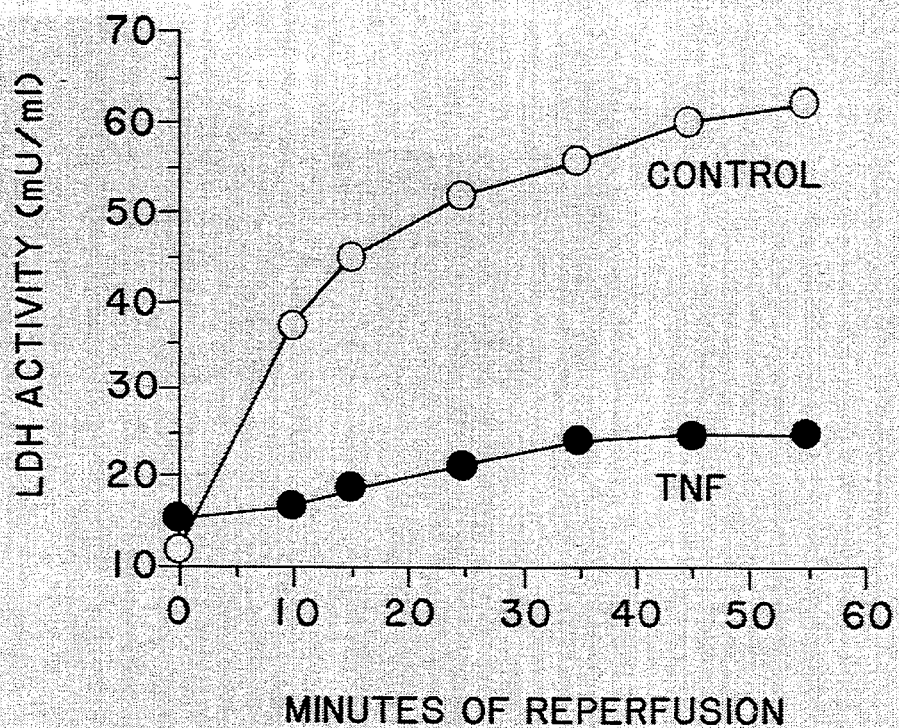
FIG. 1 shows that TNF pretreatment protects against heart damage due to ischemia and reperfusion.
FIG. 2 shows the induction of MnSOD in ischemic rat hearts pretreated with TNF prior to reperfusion.

Tumor necrosis factor or TNF, as employed herein, refers in general to the various forms of TNF which exhibit one or more biologic properties of tumor necrosis such as tumor cell lysis, inhibition of infectious agents, MHC antigen induction, and neutralization by antibody to TNF-$\alpha$ or TNF-$\beta$ but not by antibodies to other cytokines. It is believed that gamma interferon is synergistic with TNF in anti-tumor or anti-viral assays for TNF, and may therefore be desirably administered along with TNF in the practice of this invention.

In particular, the tumor necrosis factors useful herein include TNF-$\alpha$ and TNF-$\beta$. The former is described in copending EPO Appl. EP 0 168 214 A2 together with methods for its synthesis in recombinant cell culture. Similarly, the latter (previously called lymphotoxin) and suitable recombinant synthesis methods are described in copending EPO Appl. EP 0 164 965 A2. The TNF-$\alpha$ and TNF-$\beta$ described in these applications include cytotoxic amino acid sequence and glycosylation variants which also are used herein. Of course, TNF-60 or TNF-$\beta$ from nonrecombinant sources are also useful in the practice of this invention.

TNF-$\alpha$ or TNF-$\beta$ are used alone or in admixture with one another in proportions empirically determined to exert the most effective clinical response. TNF is not species specific, so TNFs from other animal species, e.g. porcine or bovine, are useful for treatment of humans. The preferred TNF for treatment of humans is mature human TNF-$\alpha$ from recombinant microbial cell culture. The TNF ordinarily will have a cytolytic activity on susceptible L-929 murine cells of greater than about $1 \times 10^6$ units/rag, wherein a unit is defined as set forth in the above-described patent applications, the disclosures of which are incorporated by reference.

As used herein, the terms "growth hormone" or "GH" denote growth hormone produced from natural source extraction and purification, as well as by recombinant cell culture systems. "hGH" refers to human growth hormone. See, for example, U.S. Pat. No. 4,321,832, specifically incorporated by reference. The terms likewise cover biologically active human growth hormone equivalents, e.g., those differing by one or more amino acids(s) in the overall sequence. Further, the terms as used in this application are intended to cover substitution, deletion and insertion amino acid variants of GH, or post-translational modifications.

As used herein, "IL-I" denotes interleukin-1 produced from natural source extraction and purification, as well as by recombinant cell culture systems. See, for example, March et al., Nature 315:641–646 (1985)), specifically incorporated by reference. The terms likewise cover biologically active IL-1 equivalents, e.g., those differing by one or more amino acids(s) in the overall sequence. Further, the terms as used in this application are intended to cover substitution, deletion and insertion amino acid variants of IL-1, or post-translational modifications.

The mature amino acid sequences for human (H) and murine (M) DF shown in FIG. 3 are disclosed in EP 285,448, published 5 Oct. 1988 (specifically incorporated by reference herein), especially at FIG. 26, including methods for its production in recombinant cell culture. See also D. P. Gearing et al., Nucleic Acids Res. 16:9857 (1988), and N. M. Gough et al., Proc. Nat. Acad. Sci. USA 85:2623–2627 (1988). For purposes of this application, DF is defined herein as any polypeptide having (a) cytoprotective activity as defined below and (b) amino acid sequence which is homologous to either amino acid sequence of FIG. 3.

Homologous, as to DF for example, for the purposes herein means that the candidate polypeptide comprises the epitope of DF that is functional in conferring protection on experimental animals, or functionally conserved amino acid variants thereof. Identification of this epitope is a matter of routine experimentation. Most typically, one would conduct systematic substitutional mutagenesis of the DF molecule while observing for reductions or elimination of cytoprotective activity. This is commonly accomplished by sequentially substituting each residue of the native DF sequence with alanine. Preferably, the residues to be substituted will be those which are (1) identically conserved among animal species, (2) located on disulfide bonded loops, and (3) hydrophilic in nature. Domains containing more than 4 identically conserved residues among animal species and which are not found within about 3 residues of a site of glycosylation are to be preferred for mutagenesis. Preferred regions for mutagenesis are 12–25, 34–60 and 121–143 of the FIG. 3 sequences. In any case, it will be appreciated that due to the size of DF most substitutions will have no effect on DF activity, but if some effect is seen it will be modestly agonistic or antagonistic. The great majority of DF variants will possess at least some cytoprotective activity, particularly if the substitution is conservative. Conservative substitutions are substitutions from the same classes, defined as acidic (Asp, Glu), hydroxy-like (Cys, Ser, Thr), amides (Asn, Gln), basic (His, Lys, Arg), aliphatic-like (Met, Ile, Leu, Val, Gly, Ala, Pro). and aromatic (Phe, Tyr, Trp). The 9 C-terminal hydrophobic residues should only be substituted, if at all, with other hydrophobic residues. The first 3 N-terminal residues may be deleted or freely substituted, and may include a serine residue inserted at the N-terminus.

Alternatively, or in addition, the active site is identified by raising antibodies against the intact native DF, screening for neutralizing antibodies, and determining the site to which the neutralizing antibodies bind. Neutralizing antibodies against DF also would find use in diagnostic immunoassays for DF, especially when used in a sandwich-type immunoassay in concert with a non-neutralizing antibody directed against another DF epitope.

Homologous sequences generally will be greater than about 30 percent homologous on an identical amino acid basis, ignoring for the purposes of determining homology any insertions or deletions from the candidate molecule in relation to either native sequence of FIG. 3. Homologies of about 50, 70 and 90% are also included within the scope hereof so long as the molecules possess the requisite cytoprotective activity.

The cytoprotective agents discussed herein, e.g. DF, GH, TNF, IL-1, also includes glycosylation variants as well as unglycosylated forms of the agents, fusions of the agents with heterologous polypeptides, and fragments of the agents, again so long as the variants possess the requisite cytoprotective activity.

The formulations may contain compounds previously suggested for use in the treatment of the conditions and diseases described herein, as well as those compounds previously suggested for use in preventing damage from ROS. Antioxidants, such as ascorbate, fibrinolytic agents such as tissue plasminogen activator, and other compounds previously suggested for use in preventing reperfusion injury may also be included. Agents that block the toxicity of high doses of TNF and/or IL-1—such as glucocorticoids and indomethacin—without altering the MnSOD-inducing activity of TNF-are also utilized in the practice of this invention. Agents which block induction of MHC antigens are also desirably administered. Compounds which effect the redox potential of ROS may also be utilized in a formulation. The protective agent(s) also is suitably formulated together with known agents in order to modify or enhance half-life or therapeutic activity. These other agents or therapies are used at the same time as the TNF, IL-I, GH and/or DF is administered or in a sequential course of therapy.

The TNF, DF, GH, and/or IL-1 are placed into sterile, isotonic formulations together with required cofactors. Formulations may contain one or more protective agents. The formulations are preferably liquid, and ordinarily a physiologic salt solution or dextrose solution, together with conventional stabilizers and/or incipients. Compositions may also be provided as lyophilized powder for ultimate delivery in solution. Saline is a suitable carrier, although other conventional parenteral solutions or buffers are usable.

In a pharmacologic sense, in the context of the present invention, a therapeutically effective amount of TNF, DF, GH, and/or IL-1 refers to that amount effective to protect normal cells from the deleterious effects of ROS. It has been discovered that TNF and/or IL-1 plus GH, and TNF and/or IL-1 plus DF provide synergistic protection against oxygen free-radical damage such as caused by hyperoxia, and thus relatively smaller dosages of a particular agent may be administered (See FIGS. 4 and 5).

Although it is currently believed that induction of MnSOD is not sufficient to protect cells from damage, monitoring of its induction by TNF is a convenient indication of TNF activity under this invention. As shown in FIG. 2, TNF induces MnSOD in ischemic rat hearts pretreated with TNF before reperfusion.

The therapeutically effective dosage of TNF to be administered to a human patient or human tissue generally will range from about 1–250 $\mu g/m^2$ per dose, and preferably from about 1–10 $\mu g/m^2$, and most preferably $10\mu g/m^2$, although the dose of the TNF administered will be dependent upon the species of the patient, the properties of the TNF employed, e.g. its activity and biological half-life, the concentration of the TNF in the formulation, the rate of dosage, the clinical tolerance of the patients involved, the pathological condition of the patients and the like, as is well within the skill of the physician. It will be appreciated that the practitioner will adjust the therapeutic dose in line with clinical experience for any given TNF. Preferably, the TNF is administered intravenously or intramuscularly.

The amount of DF, GH, TNF and/or IL-I which is used will depend upon the therapeutic protocol, considering the use of hyperoxia, irradiation or chemotherapy, the condition of the patient, the activity of the agent used, the administration route, and other influences that will be appreciated by the ordinary artisan. In mice, a dosage of about 7.5 micrograms of DF ip/mouse is acceptable, with about 0.5 micrograms to 20 micrograms per day being the range from the lowest level that is marginally effective for cytoprotection to a safe and adequate upper limit. Obviously, the dose will differ for other animals and humans and will vary depending upon administration routes. Treatment effective amounts of IL-1 administered to mice range between about 0.5 to 25 nanograms per gram of body weight of mouse.

For hGH, a suitable dosage for human administration ranges from 0.001 mg per kg of bodyweight per day to about 0.2 mg per kg of bodyweight per day. Generally, daily dosages of GH will be from about 0.05 mg per kg of bodyweight per day. Normally, from 0.07 to 0.15 mg/kg, in one or more applications per day, is effective to obtain the desired result. In an alternative approach, the GH, particularly where formulated in a timed-release form, may be administered less frequently, i.e., every other day or every third day for certain indications. It is presently preferred the GH be administered within 0 to 24 hours following exposure to free-radical injury.

In the practice of this invention, compositions which include a therapeutically effective amount of TNF, DF, GH, and/or IL-1 are administered to patients having or at risk for damage from ROS. Accordingly, in some embodiments of this invention, the protective agent, alone or with other agents as described above, is administered to a patient within a temporal period, most preferably within 24 hours prior, preferably prior to or concurrent with, or shortly following exposure, to ROS. In the case of reperfusion, exposure to the ROS may be predetermined and deliberate, or may be a consequence of other therapeutic measures.

In other embodiments, a patient's ROS exposure is of a more chronic or regular nature, as with certain of the diseases and chronic conditions described above. In these situations, the protective agent(s) may be administered as part of a long-term course of therapy.

Some embodiments deal with the transfer to and implantation of tissues, and the complex tissues known as organs, in a recipient patient. For purposes of this invention, the term "tissues" shall be understood to include, without limitation, muscle tissue, connective tissue, epithelial tissue, nervous tissue, vascular tissue, bone, brain, reproductive organs, respiratory organs, digestive organs, excretory organs, urinary organs, sensory organs, and skeletal muscle organs. Particularly preferred tissues include heart, lung, kidney, liver, skin and bone grafts. Suitable tissues are synthetic as well as those which are removed from a donor.

For tissues to be removed from a donor prior to their transfer to and implantation in a patient, treatment with TNF, GH, DF, and/or IL-1 may be a accomplished in several different ways. The protective agent(s) may be administered to the donor, as described above. Alternatively, the tissue itself may be treated, either prior to or after removal from the donor, and either prior to or after transfer to the patient, but most preferably prior to or concurrent with reperfusion.

Since the first successful human orthotopic liver transplant by Starzi in 1967, methods for the transplant of tissues, as well as suitable protocols for their perfusion with various agents, have become commonly known in the art. Suitable protocols and perfusion solutions are described, for example, in Kalayoglu et al., The Lancet, Mar. 19, 1988, pp. 617-619. Perfusion is commonly accomplished with a mechanical pump, as described in Example I below. Suitable perfusion solutions include lactated Ringer's solution, UW solution, and pharmaceutically acceptable isotonic solutions. These solutions enable a TNF. DF, GH, and/or IL-1-treated tissue to be preserved by continuous perfusion or cold storage until it is implanted into a recipient patient.

In an embodiment of this invention, perfusion solutions are provided, comprising TNF, DF, GH and/or IL-1 at concentrations of approximately 1-250 $\mu g/m^2$ with a pharmaceutically acceptable isotonic solution.

For each type of type of disease or injury, and for each animal species to be treated, the exact protective TNF, DF, GH, and/or IL-1 dosage necessary for this protective effect may vary from that shown herein, and the exact administration parameters suitable for any given patient or animal species will be determined by routine experimentation. Typically, the patient or tissue is first administered the agent, e.g. by intravenous or intramuscular administration, and thereafter exposed to ROS. The patient or tissue is monitored for symptoms of any beneficial or deleterious effects of the treatment. If the initial treatment is partially successful or unsuccessful, the process may be repeated, optionally with a modification of the dosage or route of administration.

According to this invention, patients from differing species are all treated by the pharmaceutically acceptable administration of TNF, DF, GH, and/or IL-1 in a pharmaceutically effective dosage and for a period of time sufficient to inhibit, prevent, protect from the damaging effects of ROS.

It is also envisioned that, in the practice of this invention, administration of the protective agent(s) may by accompanied by the therapeutic administration of a course of radiation, heat, and/or ROS inducing agents. The agent, alone or with other agents, may be administered to a patient prior to, following, or simultaneously with exposure to radiation, heat, or ROS inducing agents. Exposure to the radiation, heat, or ROS inducing agents may be predetermined and deliberate, or may be a consequence of other therapeutic measures. Heat or ROS-inducing agents may be administered with radiation, and/or with an additional dose of TNF, DF, GH and/or IL-1.

ROS inducing agents and their methods of administration are described above. Radiation and heat are administered by protocols commonly known to practitioners, as described in the literature cited above. Typically, radiation is given in pulses over a period of time from 1-8 weeks, for a total dose of approximately 1000-1200 rads. Heat may be administered by known methods such as a heat blanket or hyperthermia chamber, for a period sufficient to raise a patient's body tissue temperature above 37° C., preferably 40°-45° C., and most preferably to approximately 42° C.

Where GH alone is administered to a patient having or at risk of hyperoxia damage, the patient is may be subjected to atmospheric conditions with greater levels of oxygen than normal atmospheric conditions.

In order that the invention described herein may be more fully understood, the following examples are set forth. It should be understood that these examples are for illustrative purposes only, and are not to be construed as limiting this invention in any manner.

EXAMPLE 1

The effect of TNF on isolated rat heart

This experiment was conducted by Dr. Lynn Eddy at the University of Southern California. Healthy Sprague Dawley rats weighing between 200 and 300 g are anesthetized with sodium pentobarbital. 30 mg/kg, intraperitoneally. Heparin (500 U) is administered intravenously. The chests are opened and the hearts rapidly excised and placed in iced cold buffer until they stop beating. The hearts are mounted by the aortic roots to a stainless steel cannula and perfused through the aorta in a retrograde manner (Langendorff). Krebs-Henseleit buffer of the following composition is used throughout the experiments (final concentration in mM/L): NaCI, 118; KCI, 4.7; CaCI, 2.5; MgSO, 1.2; KH PO, 1.2; Ca-EDTA, 0.5; NaHCO, 25; and glucose, 10. The buffer is aerated with 95 % 0-5% CO. Perfusion is maintained by a peristaltic pump at a flow rate of 10 ml/min and perfusion pressure is monitored by a P23AA Statham pressure transducer attached to a side arm of the aortic inflow cannula and recorded on a Hewlett Packard 7702B recorder. The complete perfusion system is maintained within a thermostatically controlled plexiglass chamber maintained at 37° C.

The hearts are perfused 3-4 minutes to remove blood. After a 20 minute control period, global ischemia is initiated by stopping the pump and turning off the 95% 0-5% CO. At the end of the ischemic period, the pump is restarted and the buffer reoxygenated.

Enzyme leakage from the heart cells is determined in effluent samples collected from the heart at specific time periods during the control period and during reperfusion. Lactic dehydrogenase (LDH) activity is assayed by monitoring the oxidation of NADH, using pyruvate as the substrate. NADH is monitored at 340 nm using a Perkin Elmer Lambda 3 recording spectrophotometer. As shown in FIG. 1, LDH activity from hearts treated with 101$\mu$g TNF compared to controls indicates that the TNF protected the heart from damage mediated by its ischemia and reperfusion.

EXAMPLE 2

This experiment was conducted by Dr. Min-Fu Tsan, at the Department of Veterans Affairs Medical Center in Albany, New York. The effects of TNF-alpha, TNF-beta, IL-1 beta, interferon (IFN)-gamma, growth hormone and DF, alone and in various combinations, on the protection of rats against oxygen toxicity was examined.

Tracheal insufflation of the cytoprotective agent and the exposure of the rats to hyperoxia was performed essentially as described in Tsan et al., J. Appl. Physiol. 68: 1211-1219, 1990. Briefly, male Sprague-Dawley rats (Harlan Sprague Dawley, Altamont, NY, USA) free of respiratory infections and weighing between 250-350 g, were anesthetized with methoxyflurane (Pittman-Moore Inc., Washington Crossing, N.J., USA) and were intubated with a 16 G i.v. catheter (Angiocath, Becton Dickinson, Sandy, Utah, USA). One ml of the protective agent(s) (agents and concentrations are shown in the next paragraph) was administered to the rats in calcium-magnesium free Hanks' balanced salt solution (HBSS) (or 1 ml HBSS for control animals) followed by 2 ml of air, injected through the intratracheal catheter. Ascultation of the chest with a stethascope was done to insure that the agent was insufflated into the lungs. After the rats had recovered from the effect of anesthesia, they were placed in groups of 5 in a lucite chamber (45 by 40 by 25 $cm^3$) which was flushed with 100% $O_2$ at 15 liter/rain for 5 rain and then maintained at 5 liter/min. The concentration of $O_2$ in the chamber as monitored using an oxygen analyzer (Hudson Oxygen Analyzer, Ventronics Products Division, Temecula, Calif., USA) was more than 95% at all times. The rats were given free access to water and diet. Control exposure (normoxia) was performed in room air.

Figure 4A:
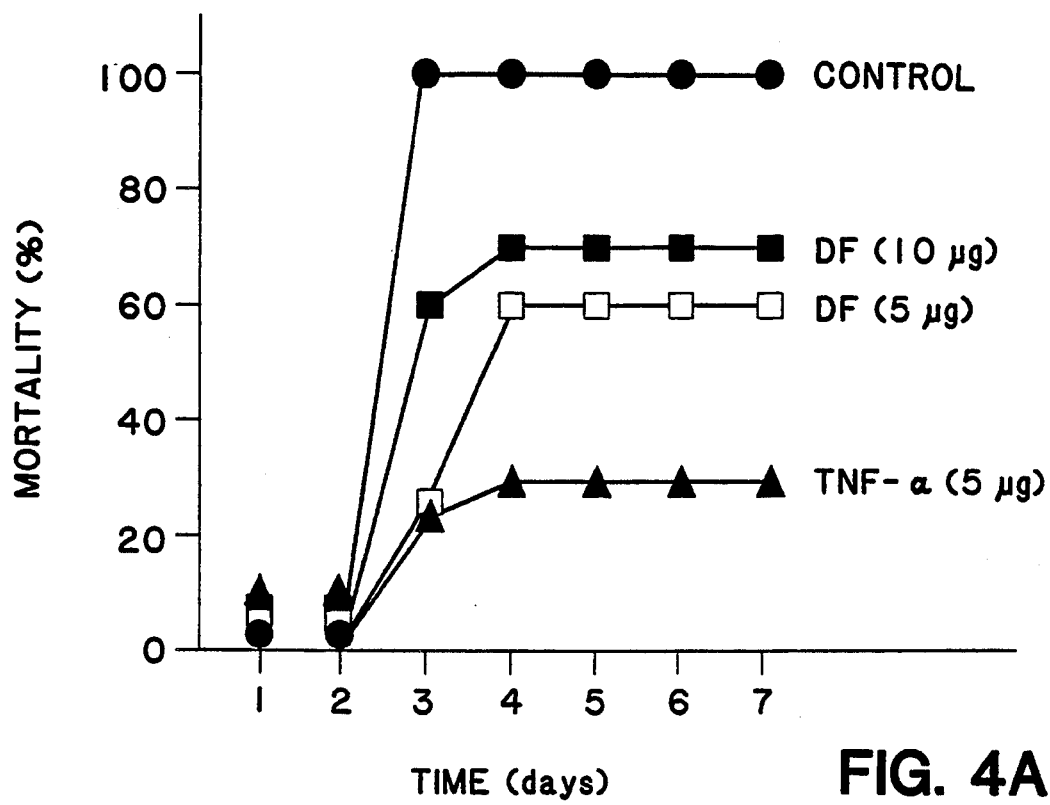
FIG. 4A illustrates the results obtained in Example 2, showing that TNF-$\alpha$ and DF protect adult rats from oxygen toxicity.
Figure 4B:
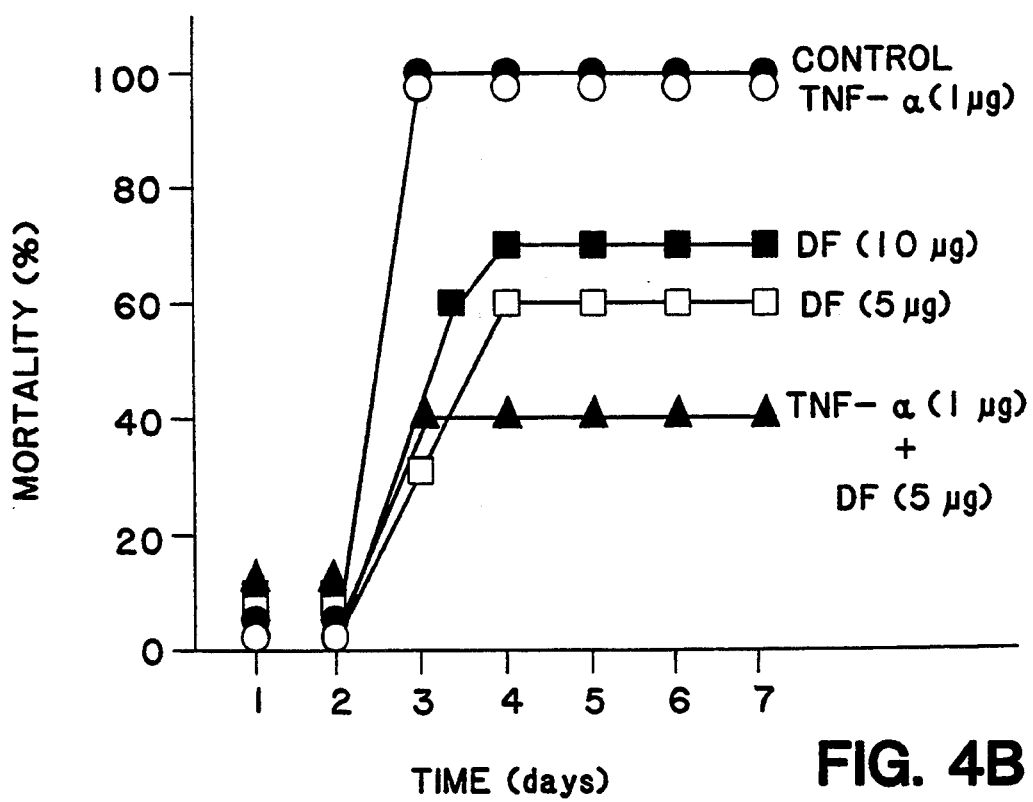
FIG. 4B shows the synergistic effect of DF plus TNF.
Figure 5:
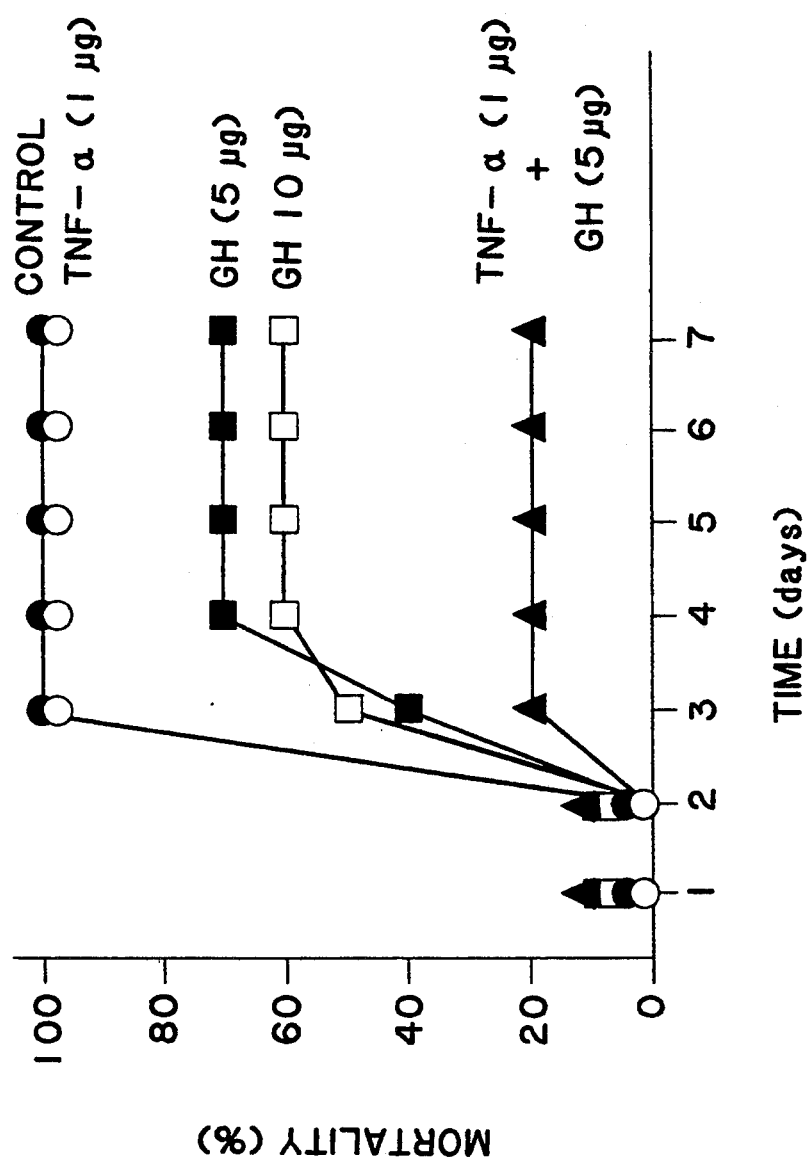
FIG. 5 illustrates the results obtained in Example 2, showing that TNF$\alpha$ and GH protect adult rats from oxygen toxicity.

Results are shown in FIGS. 4 and 5, and the percent survival after 3 days and 7 days are shown below.

| Tracheal insufflate | n | 3 days | 7 days |
|---|---|---|---|
| HBSS (control) | 45 | 0 | 0 |
| DF 5 μg | 10 | 70 | 40 |
| DF 10 μg | 10 | 40 | 30 |
| GH 5 μg | 15 | 53 | 27 |
| GH 10 μg | 10 | 50 | 40 |
| TNF-α 5 μg | 17 | 76 | 71 |
| TNF-α 1 μg | 10 | 0 | 0 |
| DF 5 μg + TNF 1 μg | 15 | 100 | 93 |
| GH 5 μg + TNF 1 μg | 15 | 67 | 67 |

In data not shown, IL-1 was also protective comparable to TNF. It may be seen from these results that TNF or IL-1 alone are effective in preventing death due to hyperoxia. Growth Hormone and DF are less effective for the same purpose when used alone, but synergize with TNF and/or IL-1 in protecting the animals. This work indicates that these agents be used in any hyperbaric treatment, including oxygen treatment of premature infants and cancer patients.

EXAMPLE 3

Figure 6:
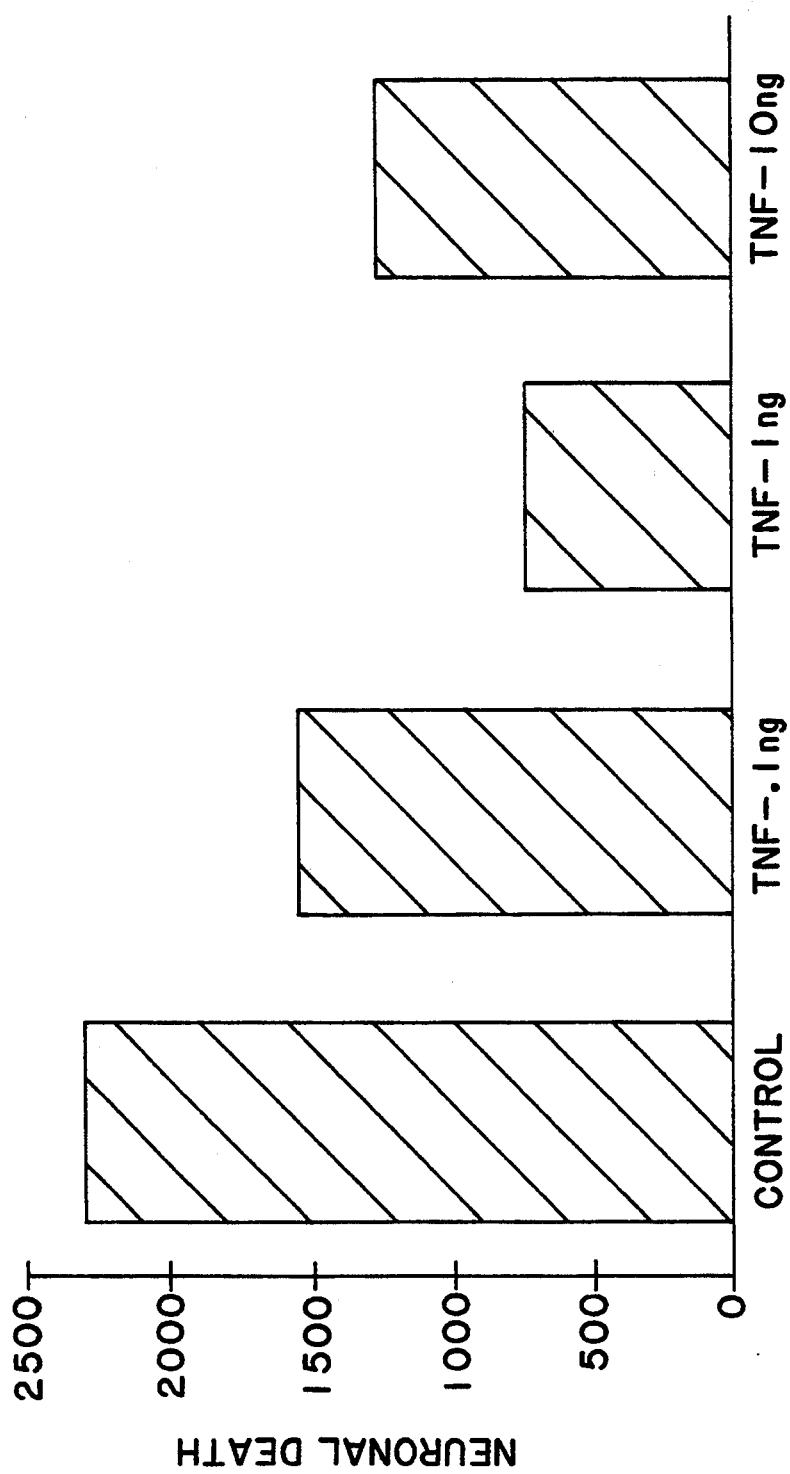
FIG. 6 shows the protective effect of TNF on neuronal survival after glucose deprivation. The number of neurons dying under each condition (10,000 total neurons per dish) are shown.

This experiment was conducted by Dr. John A. Kessler, at the Albert Einstein College of Medicine of Yeshiva University, New York N.Y. The protective effect of TNF on neuronal survival after glucose deprivation (analogous to nutrient depletion following ischemia) was studied according to the method of Saez et al., Proc. Natl. Acad. Sci. USA 84: 3056-3059, 1987. As shown in FIG. 6, TNF was found to give a strongly protective effect: maximal effects are shown at 1 ng/ml of TNF.

---

I claim:

1. A method for prophylaxis and treatment of the deleterious effects of reactive oxygen species, comprising the administration to a patient of a cytoprotective amount of at least one cytoprotective agent selected from the group consisting of (a) D-factor (DF), (b) tumor necrosis factor-α (TNF-α) plus GH, and (c) tumor necrosis factor-α (TNF-α) plus DF.

2. The method of claim 1, wherein said patient has or a condition selected for the group consisting of reperfusion injury, bronchopulmonary dysplasia, stroke, arteriolosclerosis, atherosclerosis, myocardial infarct, sepsis, acquired immunodeficiency syndrome, diabetes, multiple sclerosis, inflammation-induced arthritis, hyperbaric treatment of premature birth, hyperoxia, transplant rejection or transplantation injury, sickle cell anemia, sickle cell trait, hyperbaric cancer treatment, alcoholic or non-alcoholic cirrhosis, bleomycin-induced lung fibrosis, synovial inflammation induced by bacterial LPS endotoxin, lung injury resulting from immune complexes, and Parkinson's disease.

3. The method of claim 1, wherein said patient is a mammal.

4. The method of claim 1, wherein alpha, beta, or gamma-interferon is also administered.

5. The method of claim 1 (c) or (d) wherein, approximately 1–250 μg/m² of said TNF-α is administered.

6. The method of claim 1, wherein said cytoprotective agent(s) is administered along with a fibrinolytic agent or antioxidant.

7. The method of claim 1, wherein said patient is at risk for reperfusion injury, and said cytoprotective agent is administered prior to reperfusion.

8. The method of claim 1, wherein said administration is not followed by the administration of therapeutic doses of heat, radiation, or reactive oxygen species inducing agents.

9. A method for the protection of ischemic tissues, comprising the administration to said tissue prior to reperfusion of a cytoprotective amount of at least one cytoprotective agent selected from the group consisting of (a) growth hormone (GH), (b) D-factor (DF), (c) tumor necrosis factor-$\alpha$ (TNF-$\alpha$) plus GH, and (d) tumor necrosis factor-$\alpha$ (TNF-$\alpha$) plus DF.

10. The method of claim 9, wherein said cytoprotective agent(s) is administered prior to or after removal of said tissue from a donor.

11. The method of claim 9, wherein said cytoprotective agent is administered prior to or after transfer of said tissue to a patient.

12. The method of claim 9, wherein said tissue has been or is to be removed from a mammalian donor and transferred into a mammalian patient.

13. The method of claim 9, wherein alpha, beta, or gamma-interfection is also administered.

14. The method of claim 9 (d) or (d), wherein approximately 1–250 $\mu g/m^2$ of said TNF-$\alpha$ is administered.

15. The method of claim 9, wherein said cytoprotective agent(s) is perfused into said tissue by mechanical means.

16. The method of claim 9, wherein said cytoprotective agent(s) is continuously perfused through said tissue with a pharmaceutically acceptable excipient.

17. The method of claim 16, wherein said cytoprotective agent(s) is perfused into said tissue before or after the tissue has been removed from a donor but prior to the implementation of said tissue into a patient, and wherein said cytoprotective agent(s) is replaced by an isotonic perfusion fluid free of said cytoprotective agent(s) immediately prior to implantation of the tissue into said patient.

18. The method of claim 9, wherein said cytoprotective agent(s) is administered along with an antioxidant or fibrinolytic agent.

19. The method of claim 9, wherein said tissue is selected from the group consisting of muscle tissue, connective tissue, epithelial tissue, nervous tissue, vascular tissue, bone, brain, reproductive organs, respiratory organs, digestive organs, excretory organs, urinary organs, sensory organs, and skeletal muscle organs.

20. A method for the prophylaxis or treatment of the deleterious effects of reactive oxygen species on tissue to be removed from a donor and transferred to a patient, comprising the administration to said donor prior to the removal of said tissue of a cytoprotective amount of at least one cytoprotective agent selected from the group consisting of (a) growth hormone (GH), (b) D-factor (DF), (c) tumor necrosis factor-$\alpha$ (TNF-$\alpha$) plus GH, and (d) tumor necrosis factor-$\alpha$ (TNF-$\alpha$) plus DF.

21. The method of claim 20, wherein alpha, beta, or gamma-interferon is also administered.

22. The method of claim 20, wherein said cytoprotective agent(s) is administered to said donor intravenously.

23. The method of claim 20, wherein said cytoprotective agent(s) is administered along with an antioxidant or fibrinolytic agent.

24. The method of claim 20, wherein said tissue is selected from the group consisting of muscle tissue, connective tissue, epithelial tissue, nervous tissue, vascular tissue, bone, brain, reproductive organs, respiratory organs, digestive organs, excretory organs, urinary organs, sensory organs, and skeletal muscle organs.

* * * * *

UNITED STATES PATENT AND TRADEMARK OFFICE
CERTIFICATE OF CORRECTION

PATENT NO. : 5,370,870
DATED : December 6, 1994
INVENTOR(S) : Grace H. W. Wong

It is certified that error appears in the above-indentified patent and that said Letters Patent is hereby corrected as shown below:

On the title page: Item [57] Column 1, line 1

In the abstract, please change "protection inhibtion" to read --protection, inhibition--.

In column 1, line 68, please change "cylosol" to read --cytosol--.

In column 3, line 13, please change "designated $\beta$" to read --designated $\alpha$--.

In column 13, claim 2, line 61, following "patient has or", please insert --is at risk of having--.

In column 13, claim 2, line 62, please change "for" to read --from--.

In column 15, claim 14, line 26, please change "9(d)" to read --9(c)--.

Signed and Sealed this

Fourth Day of April, 1995

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 179 amino acids
        ( B ) TYPE: amino acid
        ( D ) TOPOLOGY: linear ( x i ) SEQUENCE DESCRIPTION: SEQ ID NO:1:

```
Pro  Leu  Pro  Ile  Thr  Pro  Val  Asn  Ala  Thr  Cys  Ala  Ile  Arg  His
 1              5                        10                       15

Pro  Cys  His  Asn  Asn  Leu  Met  Asn  Gln  Ile  Arg  Ser  Gln  Leu  Ala
              20                        25                       30

Gln  Leu  Asn  Gly  Ser  Ala  Asn  Ala  Leu  Phe  Ile  Leu  Tyr  Tyr  Thr
              35                        40                       45

Ala  Gln  Gly  Glu  Pro  Phe  Pro  Asn  Asn  Leu  Asp  Lys  Leu  Cys  Gly
              50                        55                       60

Pro  Asn  Val  Thr  Asp  Phe  Pro  Pro  Phe  His  Ala  Asn  Gly  Thr  Glu
              65                        70                       75

Lys  Ala  Lys  Leu  Val  Glu  Leu  Tyr  Arg  Ile  Val  Val  Tyr  Leu  Gly
              80                        85                       90

Thr  Ser  Leu  Gly  Asn  Ile  Thr  Arg  Asp  Gln  Lys  Ile  Leu  Asn  Pro
              95                       100                      105
```

```
Ser Ala Leu Ser Leu His Ser Lys Leu Asn Ala Thr Ala Asp Ile
            110                 115                     120
Leu Arg Gly Leu Leu Ser Asn Val Leu Cys Arg Leu Cys Ser Lys
            125                 130                     135
Tyr His Val Gly His Val Asp Val Thr Tyr Gly Pro Asp Thr Ser
            140                 145                     150
Gly Lys Asp Val Phe Gln Lys Lys Leu Gly Cys Gln Leu Leu
            155                 160                 165
Gly Lys Tyr Lys Gln Ile Ile Ala Val Leu Ala Gln Ala Phe
            170                 175                 179
```

( 2 ) INFORMATION FOR SEQ ID NO:2:

( i ) SEQUENCE CHARACTERISTICS:
        ( A ) LENGTH: 179 amino acids
        ( B ) TYPE: amino acid
        ( D ) TOPOLOGY: linear ( x i ) SEQUENCE DESCRIPTION: SEQ ID NO:2:

```
Pro Leu Pro Ile Thr Pro Val Asn Ala Thr Cys Ala Ile Arg His
  1             5                  10                     15
Pro Cys His Gly Asn Leu Met Asn Gln Ile Lys Asn Gln Leu Ala
            20                  25                     30
Gln Leu Asn Gly Ser Ala Asn Ala Leu Phe Ile Ser Tyr Tyr Thr
            35                  40                     45
Ala Gln Gly Glu Pro Phe Pro Asn Asn Val Glu Lys Leu Cys Ala
            50                  55                     60
Pro Asn Met Thr Asp Phe Pro Ser Phe His Gly Asn Gly Thr Glu
            65                  70                     75
Lys Thr Lys Leu Val Glu Leu Tyr Arg Met Val Ala Tyr Leu Ser
            80                  85                     90
Ala Ser Leu Thr Asn Ile Thr Arg Asp Gln Lys Val Leu Asn Pro
            95                 100                    105
Thr Ala Val Ser Leu Gln Val Lys Leu Asn Ala Thr Ile Asp Val
            110                115                    120
Met Arg Gly Leu Leu Ser Asn Val Leu Cys Arg Leu Cys Asn Lys
            125                130                    135
Tyr Arg Val Gly His Val Asp Val Pro Pro Val Pro Asp His Ser
            140                145                    150
Asp Lys Glu Ala Phe Gln Arg Lys Lys Leu Gly Cys Gln Leu Leu
            155                160                165
Gly Thr Tyr Lys Gln Val Ile Ser Val Val Val Gln Ala Phe
            170                175                179
```